(12) United States Patent
Chen et al.

(10) Patent No.: US 8,691,789 B2
(45) Date of Patent: Apr. 8, 2014

(54) PROBE OF IODINE-123 MARKER THYMIDINE (FLT)ANALOGUE [$^{123}$I]-IARAU

(71) Applicant: Atomic Energy Council-Institute of Nuclear Research, Taoyuan County (TW)

(72) Inventors: Jenn-Tzong Chen, Taipei (TW); Ho-Lien Huang, Taoyuan County (TW); Jia-Rong Chen, Miaoli County (TW); Chung-Shan Yu, Hsinchu (TW); Wen-Chin Su, Changhua County (TW); Ching-Shiuann Yang, Taoyuan County (TW); Wuu-Jyh Lin, Taoyuan County (TW)

(73) Assignee: Institute of Nuclear Energy Research, Atomic Energy Council, Lungtan, Taoyuan (TW)

( * ) Notice: Subject to any disclaimer, the term of this patent is extended or adjusted under 35 U.S.C. 154(b) by 0 days.

(21) Appl. No.: 13/709,212

(22) Filed: Dec. 10, 2012

(65) Prior Publication Data

US 2014/0066614 A1 Mar. 6, 2014

(30) Foreign Application Priority Data

Aug. 30, 2012 (TW) .............................. 101131642 A

(51) Int. Cl.
*A01N 43/04* (2006.01)
*A61K 31/70* (2006.01)

(52) U.S. Cl.
USPC ................ 514/50; 514/43; 514/49; 536/28.1; 536/28.4; 536/28.55

(58) Field of Classification Search
None
See application file for complete search history.

(56) References Cited

PUBLICATIONS

Van Den Abbeele et al. Biophysical Aspects of Auger Processes, AAPM Symposium Series No. 8 (1992), pp. 372-395.*

* cited by examiner

*Primary Examiner* — Patrick Lewis
(74) *Attorney, Agent, or Firm* — Jackson IPG PLLC

(57) ABSTRACT

A tumor radiation probe of iodine-123 marker thymidine (FLT) analogue [$^{123}$I]-IaraU is disclosed. Commercial available uridine is used as the raw material for the synthesis of the precursor. A radioactive iodine-123 is marked on an alkaline group of uridine to obtain [$^{123}$I]-IaraU, which is distinguishable from [$^{18}$F]-FLT marking $^{18}$F on a glycosyl group to obtain a novel tumor radiation probe. The marking procedures include mixing the marker precursor with Na [$^{123}$I] solution, acetic acid and hydrogen peroxide solution, and the solution of chloroform and sodium hydroxide. The sonication time increases from 1 minute to 10 minutes, so that [$^{123}$I]-IaraU has radiologically chemical purity of higher than 98% and radiological specific activity of not less than 0.196 GBq/umole, and the yield can increase from 8% to 40%. Its radioactive specific activity, yield and purity reach to the degree for the use in biological experiments, while reducing production cost.

3 Claims, 3 Drawing Sheets

PROBE OF IODINE-123 MARKER THYMIDINE (FLT) ANALOGUE [$^{123}$I]-IARAU

BACKGROUND OF THE INVENTION

1. Field of the Invention

The present invention relates to a tumor radiation probe, particularly to a molecule similar to $^{18}$F-FLT, and more particularly to [$^{123}$I]-IaraU of iodine-123 marker thymidine (FLT) analogue.

2. Description of Related Art

Development of new gene probes for observation of gene expression can be realized by non-invasive nuclear medicine imaging to watch the effectiveness of in vivo gene therapy. Radioactive nucleosides, such as $^{18}$F-FLT, which is used to confirm the existence of tumor cells, have been widely applied in tumor imaging.

Such imaging agents used to detect cell proliferation are obtained by specific experimental procedures using special experimental apparatus in the laboratory. However, its manufacturing cost is relatively high and the obtained product is not easily purified, so that it is difficult to spread widely and therefore cannot meet the user's need in practical use.

SUMMARY OF THE INVENTION

A main purpose of this invention is to overcome the above problems and provide a novel molecule similar to $^{18}$F-FLT, specifically [$^{123}$I]-IaraU of iodine-123 marker thymidine (FLT) analogue.

It is another purpose of this invention to provide a synthesis path for [$^{123}$I]-IaraU to enhance the applications of a tumor radiation probe similar to $^{18}$F-FLT in the future.

In order to achieve the above and other objectives, the tumor radiation probe of iodine-123 marker thymidine (FLT) analogue [$^{123}$I]-IaraU according to the invention uses a commercial available uridine as the raw material for the synthesis of the precursor of [$^{123}$I]-IaraU. A radioactive iodine-123 is used for radiological marking to obtain a novel tumor radiation probe which is similar to [$^{18}$F]-FLT and makes radioactive specific activity, yield and purity reach to the degree for the use in biological experiments. By means of establishing the radioactive marker of uridine analogue, the production cost can be effectively reduced. On the other hand, the synthesized iodine-123 marker of FLT analogue is subject to in vivo cellular experiments which use cells of NG4TL4-wild type, NG4TL4-HSV tk, NG4TL4-sr39 tk. The experiments include cellular cumulative experiments at time points of 0.25, 0.5, 1.5, 3, and 5 hours. The results show that there is no significant intake of [$^{123}$I]-IaraU in these three cells. The NG4TL4-HSVtk cell has a similar nature to FLT at the previous time points, which means that both of them may enter the cell via a similar mechanism and be subject to HSV-tk phosphorylation. However, [$^{123}$I]-IaraU, unlike FLT, cannot be further subject to bi-phosphorylation, but can be discharged from the cell after hydrolysis. At the initial stage, both of them are similarity but later they are very different. Such results contribute to advanced applications on similar molecular synthesis in the future.

DETAILED DESCRIPTION OF THE PREFERRED EMBODIMENTS

The aforementioned illustrations and following detailed descriptions are exemplary for the purpose of further explaining the scope of the present invention. Other objectives and advantages related to the present invention will be illustrated in the subsequent descriptions and appended tables.

Figure 1:
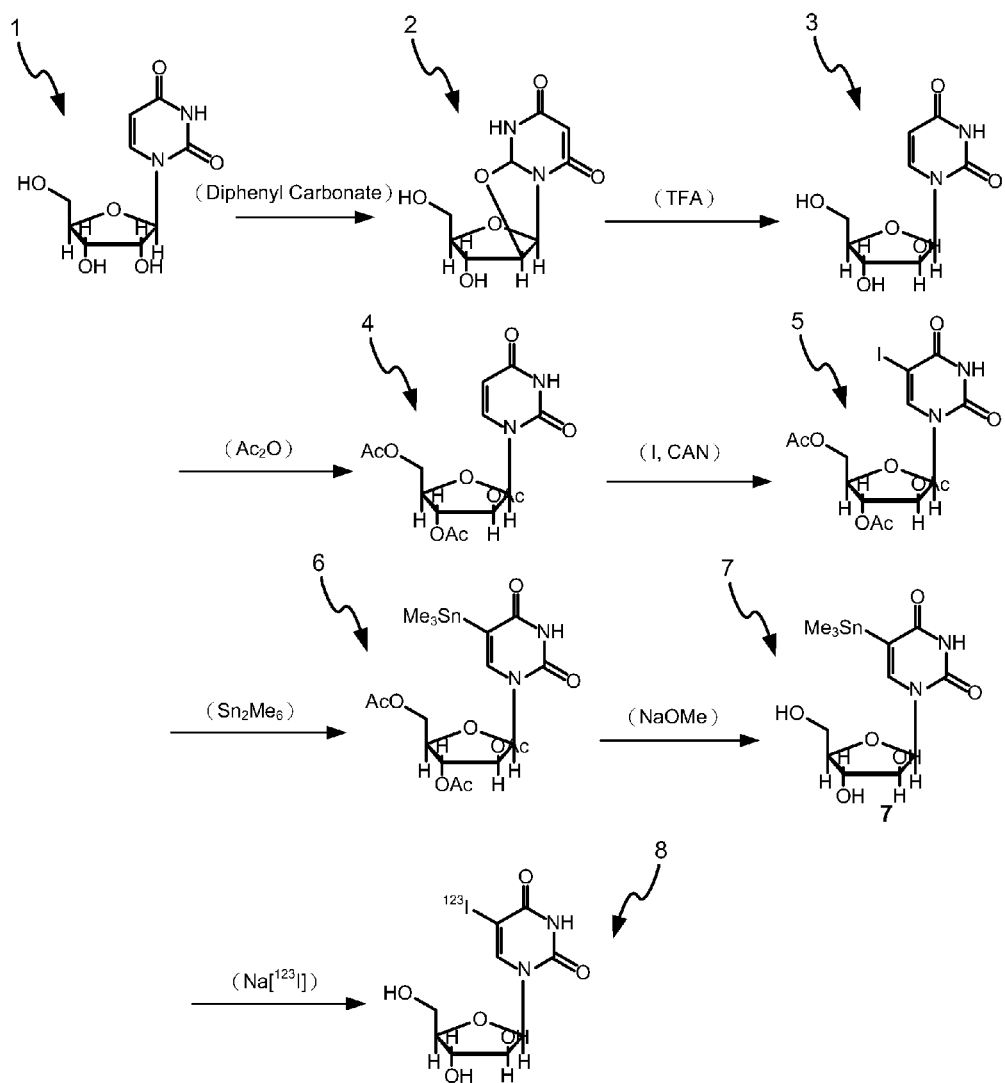
FIG. 1 is a schematic view of a synthesis reaction of [$^{123}$I]-IaraU of iodine-123 marker thymidine analogue according to the invention.
Figure 2:
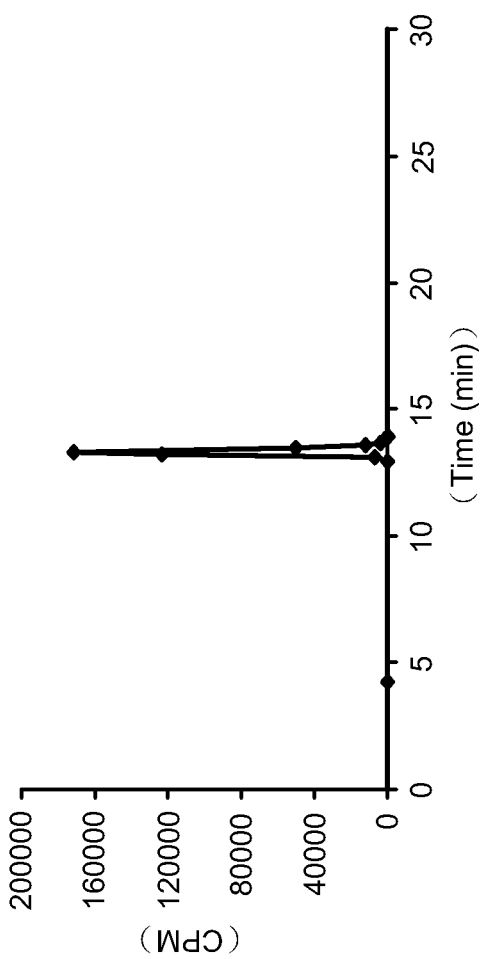
FIG. 2 is a schematic view of UV region signals by HPLC chromatography according to the invention.

FIG. 1 is a schematic view of a synthesis reaction of [$^{123}$I]-IaraU of iodine-123 marker thymidine analogue according to the invention. FIG. 2 is a schematic view of UV region signals by HPLC chromatography according to the invention. As shown: the present invention provides a probe having [$^{123}$I]-IaraU of iodine-123 marker thymidine (FLT) analogue. Commercially available uridine is taken as the raw material for the synthesis of a new probe precursor, and iodine-123 is used for radiological marking, so as to obtain a novel radiation probe of [$^{18}$F]-FLT analogue. [$^{123}$I]-IaraU has a structure as follows:

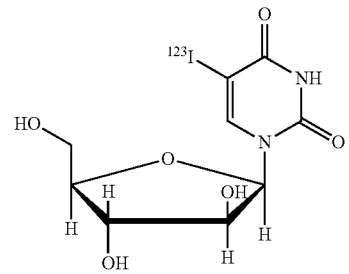

A precursor is prepared with a multi-step synthesis in advance in an organic laboratory. The radiological marking and purification are carried out using the precursor and the radiation source. When in preparation, an organic synthesis path starts at uridine 1. With the assistance of diphenyl carbonate, 2,2'-cyclouridine 2 is formed at 140° C. Then the use of dilute trifluoro acetic acid (TFA) contributes to open loops to obtain a product 3. An exposed hydroxyl group is protected with acetic anhydride (Ac$_2$O) to obtain a product 4. Next, a terminal of an alkaline group is connected to iodine to obtain a product 5. After the addition of tin, a product 6 is obtained. The protection is removed to obtain a radiological marker precursor 7. By using radioactive sodium iodide (Na [$^{123}$I]) provided by Institute of Nuclear Energy Research (INER), an iodine atom is marked at oxidizing conditions to obtain a radioactive product 8. The product 8 is a new molecule similar to $^{18}$F-FLT. In a preferred embodiment, as shown in FIG. 1 [$^{123}$I]-IaraU of iodine-123 marker FLT analogue is synthesized as follows:

Example 1

Preparatory Work $^1$H-NMR and $^{13}$C-NMR nuclear magnetic resonance spectroscopy are under operation at 500 MHz, along with mass spectrometry using an electrospray ionization method. A thin layer liquid column chromatography is used with silica gel 60 F254 precoated plates, being viewed by irradiation of 254 nanometers (nm) wavelength UV light. Rapid column chromatography is used with fillers of silica gel 60 (230~400 mesh). All solvents for reactions are used only after dehydration according to conventional procedures.

Example 2

Synthesis of 2,2'-cyclouridine 2

500 mg (2.05 mmol) of uridine 1, 570 mg of (2.65 mmol, 1.3 gram-equivalent (eq)) of diphenyl carbonate, and 10 mg (0.12 mmol, 0.059 eq) of sodium bicarbonate are dissolved in 1 mL of dimethyl formamide and heated to 140° C. After the starting materials are completely consumed, the solution is cooled down to room temperature to form white precipitates. The white precipitates are washed by ice formic acid. Residual part of the solution is removed at reduced pressure. After collection, a white powder product (2,2'-cyclouridine) 2 is obtained. Its weight and yield are 370 mg and 80%, respectively.

Mp: 250~253° C. [lit.30, 244~246° C., lit.31, 238~244° C.; commercial authentic sample: 248~251° C.]. Anal. $C_9H_{10}N_2O_5$, calcd: C, 47.79; H, 4.46; N, 12.39. found: C, 47.41; H, 4.44; N, 12.41. MW: 226.2, ESI+Q-TOF MS, M=226.1 (m/z), [M+H]+=227.1, [M+Na]+=249.0, [2M+H]+=453.2, [2M+Na]+=475.2; $^1$H-NMR (500 MHz, CD3OD): δ 3.45 (dd, $J_{5'a,4'}$=4.0, $J_{5'a,5'b}$=12.0 Hz, 1H, $H_{5'a}$), 3.49 (dd, $J_{5'b,4'}$=4.0, $J_{5'b,5'a}$=12.0 Hz, 1H, $H_{5'b}$), 4.23 (dd, $J_{4',5'a}$=4.0, $J_{4',5'b}$=4.0 Hz, 1H, $H_{4'}$), 4.54 (s, 1H, $H_{3'}$), 5.28 (d, $J_{2',1'}$=6.0 Hz, 1H, $H_{2'}$), 6.05 (d, $J_{5,6}$=7.5 Hz, 1H, $H_5$), 6.37 (d, $J_{1',2'}$=6.0 Hz, $^1$H, $H_{1'}$), 7.82 (d, $J_{6,5}$=7.5 Hz, 1H, $H_6$).

Example 3

Synthesis of 1-(β-D-arabinofuranosyl)-pyrimidin-2,4(3H)-dione 3

500 mg (2.23 mmol) of the above product 2 is taken as the starting material to immerse in 5 mL of dimethyl formamide. 70 mL of trifluoroacetic acid (0.05N) is added with continuously stirring at 80° C. The solution is concentrated under reduced pressure by removing the residual part of the solution after the completion of the reaction, and then purified by rapid column chromatography (MeOH/CHCl$_3$=1:3). A white powder product (1-(β-D-arabinofuranosyl)-pyrimidin-2,4(3H)-dione) 3 is obtained. Its weight and yield are 510 mg and 95% respectively.

Mp: 209~216° C. [lit.32, 209~211° C., lit.33, 210~215° C.]. Anal. $C_9H_{12}N_2O_6$, calcd: C, 44.27; H, 4.95; N, 11.47. found: C, 43.13; H, 5.01; N, 11.08. anal. $C_9H_{12}N_2O_6$ MW: 244.2, ESI+Q-TOF MS, M=244.1 (m/z), [M+H]+=245.0, [M+Na]+=267.1, [2M+H]+=489.2, [2M+Na]+=511.2, [3M+Na]+=755.2; $^1$H-NMR (500 MHz, CD$_3$OD): δ 3.77 (dd, $J_{5'a,4'}$=4.5, $J_{5'a,5'b}$=12.0 Hz, $^1$H, $H_{5'a}$), 3.81 (dd, $J_{5'b,4'}$=4.0, $J_{5'b,5'a}$=12.0 Hz, $^1$H, $H_{5'b}$), 3.91 (ddd, $J_{4',3'}$=3.5, $J_{4',5'b}$=4.0, $J_{4',5'a}$=4.5 Hz, $^1$H, $H_{4'}$), 4.06 (dd, $J_{3',2'}$=3.0, $J_{3',4'}$=3.5 Hz, $^1$H, $H_{3'}$), 4.14 (dd, $J_{2',3'}$=3.0, $J_{2',1'}$=4.5 Hz, $^1$H, $H_{2'}$), 5.64 (d, $J_{5,6}$=8.1 Hz, $^1$H, $H_5$), 6.12 (d, $J_{1',2'}$=4.5 Hz, $^1$H, $H_{1'}$), 7.84 (d, $J_{5,6}$=8.1 Hz, $^1$H, $H_6$).

Example 4

Synthesis of 1-(2',3',5'-Tri-O-acetyl-β-D-arabinofuranosyl)-pyrimidin-2,4-(3H)-dione 4

500 mg (2.05 mmol) of the above product 3 is taken as the starting material, and dissolved in 35 mL of pyridine. Then 11 ml of acetic anhydride is added with continuously stirring. The solution is concentrated under reduced pressure by removing the residual part of the solution after the completion of the reaction, and then purified by rapid column chromatography (acetone/n-hexane=4:5). A white product (1-(2',3',5'-Tri-O-acetyl-β-D-arabinofuranosyl)-pyrimidin-2,4-(3H)-dione) 4 is obtained. Its weight and yield are 675 mg and 89% respectively.

Mp: 128~130° C. [lit.1032, 128~130° C., lit.34, 129~130° C.]. Anal. $C_{15}H_{18}N_2O_9$, calcd: C, 48.65; H, 4.90; N, 7.56. found: C, 48.41; H, 5.01; N, 7.54. MW: 370.3, ESI+Q-TOF MS, M=370 (m/z), [M+H]+=371.1, [M+Na]+=393.0, [2M+H]+=741.1, [2M+Na]+=763.1.

Example 5

Synthesis of 1-(2',3',5'-Tri-O-acetyl-β-D-arabinofuranosyl)-5-iodopyrimidin-2,4(3H)-dione 5

454 mg (1.23 mmol) of the above product 4 as starting material, 420 mg (1.66 mmol, 1.3 eq) of iodine and 700 mg (1.27 mmol, 1 eq) of ceric ammonium nitrate are dissolved in 15 mL of anhydrous acetonitrile and heated to 80° C. After the starting material disappears, 100 mL of ethyl acetate and 30 mL (5%) of sodium bisulfate are added in turns. 30 mL of saturated saline is used to wash. After collection and combination with an organic phase, the solution is concentrated by reduced pressure. After purified by rapid column chromatography (acetone/n-hexane=2:3), a white powder product (1-(2',3',5'-Tri-O-acetyl-β-D-arabinofuranosyl)-5-iodopyrimidin-2,4(3H)-dione) 5 is obtained. Its weight and yield are 425 mg and 70% respectively.

Mp: 184~186° C. [lit.35, 185~187° C., lit.36, 184~186° C.]. Anal. $C_{15}H_{17}IN_2O_9$, calcd: C, 36.31; H, 3.45; N, 5.65. found: C, 36.09; H, 3.52; N, 5.85. anal. $C_{15}H_{17}IN_2O_9$, MW: 496.2, ESI+Q-TOF, M=496.0 (m/z), [M+H]+=497.0, [M+Na]+=519.0, [2M+H]+=993.0; 1H-NMR (500 MHz, CDCl$_3$): δ 2.04 (s, 3H, HAc), 2.13 (s, 3H, HAc), 2.17 (s, 3H, HAc), 4.19 (ddd, $J_{4',3'}$=3.5, $J_{4',5'a}$=4.5, $J_{4',5'b}$=5.5 Hz, $^1$H, $H_{4'}$), 4.38 (dd, $J_{5'a,4'}$=4.5, $J_{5'a,5'b}$=12.0 Hz, $^1$H, $H_{5'a}$), 4.44 (dd, $J_{5'b,4'}$=5.5, $J_{5'b,5'a}$=12.0 Hz, $^1$H, $H_{5'b}$), 5.10 (dd, $J_{3',2'}$=1.5, $J_{3',4'}$=3.5 Hz, $^1$H, $H_{3'}$), 5.38 (dd, $J_{2',3'}$=1.5, $J_{2',1'}$=4.0 Hz, $^1$H, $H_{2'}$), 6.27 (d, $J_{1',2'}$=4.0 Hz, $^1$H, $H_{1'}$), 7.89 (s, $^1$H, $H_6$), 8.87 (s, $^1$H, HNH).

Example 6

Synthesis of 1-(2',3',5'-Tri-O-acetyl-β-D-arabinofuranosyl)-5-trimethylstannylpyrimidin-2,4(3H)-dione 6

600 mg (1.21 mmol) of the above compound 5 as a starting material, 1.42 g (4.32 mmol, 3.6 eq) of dimethyl tin ($Sn_2Me_6$) and 22 mg (0.03 eq) of bis-triphenylphosphine palladium dichloride are dissolved in 36 mL of 1,4-dioxane, with continuously stirring at 100° C. After the starting material disappears, the solution is concentrated under reduced pressure, and then purified by rapid column chromatography (EtOAc/n-hexane=1:1). A white solid product (1-(2',3',5'-Tri-O-acetyl-β-D-arabinofuranosyl)-5-trimethylstannylpyrimidin-2,4(3H)-dione) 6 is obtained. Its weight and yield are 500 mg and 75%, respectively.

Mp: 63~73° C. anal. $C_{18}H_{26}N_2O_9Sn$, calcd: C, 40.55; H, 4.92; N, 5.25. found: C, 42.36; H, 5.79; N, 5.01. MW: 533.1, ESI+Q-TOF MS, M=532.1 (m/z), [M+H]+=533.1, [M+Na]+=555.1. Clustering of the peaks corresponding to isotope distribution of Sn was observed; $^1$H-NMR (500 MHz, $C_6D_6$): δ 0.22-0.35 (m, 9H, SnMe$_3$), 1.47 (s, 3H, HAc), 1.48 (s, 3H, HAc), 1.69 (s, 3H, HAc), 3.81 (ddd, $J_{4',3'}$=3.5, $J_{4',5'a}$=4.0, $J_{4',5'b}$=6.5 Hz, 1H, $H_{4'}$), 4.24 (dd, $J_{5'a,4'}$=4.0, $J_{5'a,5'b}$=12.0 Hz, 1H, $H_{5'a}$), 4.32 (dd, $J_{5'b,4'}$=6.5, $J_{5'b,5'a}$=12.0 Hz, 1H, $H_{5'b}$), 5.06 (dd, $J_{3',2'}$=1.0, $J_{3',4'}$=3.5 Hz, 1H, $H_{3'}$), 5.48 (dd, $J_{2',3'}$=1.0, $J_{2',1'}$=5.5 Hz, 1H, $H_{2'}$), 6.35 (d, $J_{1',2'}$=5.5 Hz, 1H, $H_{1'}$), 7.28~7.38 (m, 1H, $H_6$), 9.76 (s, 1H, HNH).

Example 7

Synthesis of 1-(β-D-arabinofuranosyl)-5-trimethyl-stannylpyrimidin-2,4(3H)-dione 7

250 mg (0.45 mmol) of the above product 6 as the starting material is dissolved in 15 mL of MeOH and cooled to 0° C. Then 5 mL of 0.01N NaOMe/MeOH is added with continuously stirring. After the starting material completely disappears, a cationic exchange resin (Dowex 500 WX8-400, H+form) is used to neutralize. After filtration, the solution is concentrated at reduced pressure at 30° C. to obtain a product (1-(β-D-arabinofuranosyl)-5-trimethylstannylpyrimidin-2,4 (3H)-dione) 7. Its weight and yield are 140 mg and 80% respectively.

$C_{12}H_{20}N_2O_6Sn$ calcd mass: 406.0 amu, ESI+Q-TOFMS, M=406.0 (m/z), [M+H]+=407.1, [M+H]+=245.1, [M+Na]+=267.1, [2M+H]+=489.2; Clustering of the peaks corresponding to isotope distribution of Sn was observed. $^1$H-NMR (500 MHz, $CD_3OD$): δ 0.24 (t, $SnMe_3$), 3.74~3.84 (m, $H_{5'}$), 3.88~3.93 (m, $H_{4'}$), 4.10 (t, J=3.5 Hz, $H_{3'}$), 4.14~4.17 (m, $H_{3'}$), 6.17 (d, $J_{1',2'}$=4.5 Hz, $H_{1'}$), 7.64 (s, $H_6$).

Example 8

Synthesis of 1-(β-D-arabinofuranosyl)-5-[$^{123}$I]iodopyrimidin-2,4(3H)-dione ([$^{123}$I]-IaraU) 8

1 mg of the above product 7 as the precursor is dissolved in 200 μL of chloroform ($CHCl_3$). 50 μL of a mixture of acetic acid and hydrogen peroxide (acetic acid/hydrogen peroxide=3:1), 0.1 ml of (0.2N) sodium hydroxide (NaOH) and 10 mCi of Na [$^{123}$I] solution are added in turns. The above mixture is diluted with 1 mL of water after sonicated for about 10 minutes. The diluted mixture is further sonicated and then stays still until stratification occurs 0.5 mL of water phase passes through $C_{18}$ and $Al_2O_3$ cartridge set, and then is washed with methanol to obtain the product ([$^{123}$I]-IaraU) 8. Collect the liquid in groups, 1 ml for each tube. After the collected liquids in third and forth tubes are mixed, the mixture is subject to purification by using high-performance liquid chromatography (HPLC). The column and gradient elution setting for HPLC are listed in the table 1 below. The times when the obtained products and standards appear are confirmed by an UV detector operated at the band of 254 nm and by a semiconductor radiation detector, as shown in FIG. 2. It is found that the times are consistent. The time when the target product ([$^{123}$I]-IaraU) 8 after HPLC separation appears a single peak is 13.7 min.

TABLE 1

Column conditions: ODS-7 RC-18 semipreparative column

| time | 50 mM pH = 5.7 phosphate buffer solution | 99.9% ethanol |
| --- | --- | --- |
| 0 min | 100% | 0% |
| 1 min | 100% | 0% |
| 11 min | 70% | 30% |
| 25 min | 70% | 30% |

Taking the cost of the synthesis experiments for the above-mentioned product [$^{123}$I]-IaraU 8 into consideration, a commercially available uridine is chosen as the starting material. In order to make the 2' terminal of hydroxy upward, the present invention converts uridine into 2,2'-cyclouridine 2 in advance. Although the general open-loop reaction is undergone at alkaline conditions, it can be done at diluted acidic conditions as well. To order to prevent any side reactions during addition of tin from being complicate, all the hydroxyl groups on a glycosyl group are protected with acetic anhydride. Since partial hydrolysis occurs while the protection is being removed, the temperature of the reaction must be reduced to 0° C. to prevent the occurrence of hydrolysis. Even so, there is still a certain proportion of the protection to be hydrolyzed, resulting in the existence of unexpected signals in the final NMR spectrum. The reaction of the radiological marker is undergone at oxidizing conditions, with high efficiency and mild environment. The experimentally prepared [$^{123}$I]-IaraU has radiologically chemical purity of higher than 98% (as shown in FIG. 2), radiological specific activity of not less than 0.196 GBq/umole, and radiation yield of about 40%.

Figure 3:
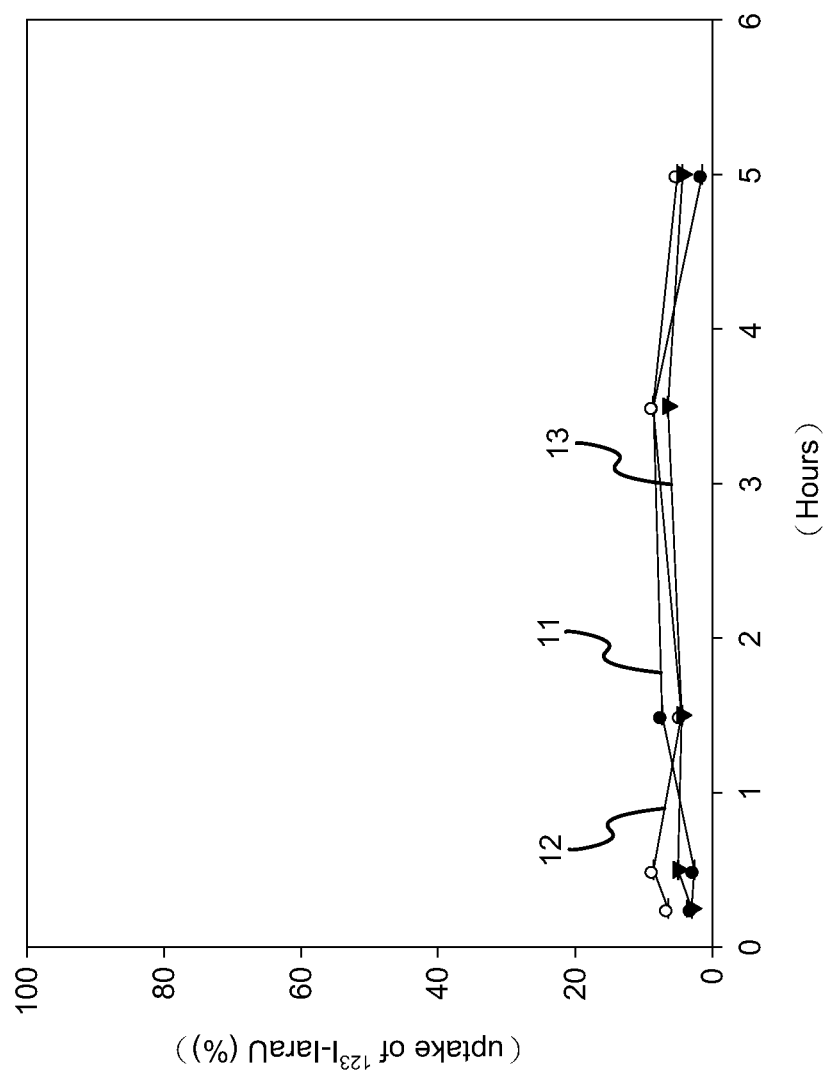
FIG. 3 is a schematic view of experimental results of cell absorption for [$^{123}$I]-IaraU according to the invention.

Please refer to FIG. 3 which is a schematic view of experimental results of cell absorption of [$^{123}$I]-IaraU according to the invention. As shown, the present invention utilizes the above synthesized iodine-123 marker FLT analogue for in vitro experiments which totally use cells of NG4TL4-wild type, NG4TL4-HSVtk, NG4TL4-sr39tk. They are cultivated in the DMEM (Dulbecco's Modified Eagle's Medium) medium containing 10% fetal bovine serum at 37° C. and in the environment having 5% carbon dioxide. Then they are planted in 96-well plate at the proportion of $1\times10^5$ cells/well for 12 hours, and then subjected to biological experiments.

Before the cellular uptake experiment starts, 1 mCi of the above [$^{123}$I]-IaraU 8 or [$^{18}$F]-FLT (from INER) is thoroughly mixed with 50 ml of serum-free DMEM medium. The cultivated medium on the 96-well plate is drained out, and the aforementioned cultivated medium mixed with radioactive material is immediately added material with the ratio of 200 μl/well. The cells to which the cultivated medium has been added are placed back to an incubator of 5% $CO_2$ at 37° C. At time points of 0.25, 0.5, 1.5, 3 and 5 hours, supernatants are collected to respectively add to 50 ul of pancreas protease EDTA mixture (Trypsin-EDTA) and then wait for 5 minutes. The solutions containing cell debris are taken for individual collection. Finally, a Gamma-Counter is used to measure the radioactivity of cytoplasm for each individual supernatant. The formula for analysis is as follows:

(Radioactivity of cytoplasm/Activity as whole)×100%.

In cellular uptake experiments, as shown by the curves 11, 12, 13 of [$^{123}$I]-IaraU in the cells of NG4TL4-wild type, NG4TL4-HSVtk and NG4TL4-sr39tk, it is found that [$^{123}$I]-IaraU in three kinds of cells has no significant increase in quantity. Even after five hours, the maximum intake is still not more than 10% of the total amount. Surprisingly, the NG4TL4-HSVtk cell has a similar nature to FLT at the previous time points, which means that both of them may enter the cell via a similar mechanism and be subject to HSV-tk phosphorylation. However, [$^{123}$I]-IaraU, unlike FLT, cannot be further subject to bi-phosphorylation, but can be discharged from the cell after hydrolysis. At the initial stage, both of them are similarity but later they are very different. Such results contribute to advanced applications on similar molecular synthesis in the future.

The present invention uses uridine as the raw material for the synthesis of the precursor of [$^{123}$I]-IaraU. At the mild conditions, radioactive iodine-123 is marked on the alkaline group to obtain [$^{123}$I]-IaraU, which is distinguishable from [$^{18}$F]-FLT marking $^{18}$F on the glycosyl group. Thereby, a novel tumor radiation probe is obtained.

The marking procedures include mixing the marker precursor with Na [$^{123}$I] solution, acetic acid and hydrogen peroxide solution, and the solution of chloroform and sodium hydroxide. The sonication time increases from 1 minute to 10 minutes, so that the yield can increase from 8% to 40%. Therefore, its radioactive specific activity, yield and purity can reach to the degree for the use in biological experiments. Although [$^{123}$I]-IaraU with [$^{18}$F]-FAU is very similar in structure, [$^{123}$I]-IaraU is not obvious in the cell uptake experiments. With the comparison of the metabolic mechanism of molecules having similar structures and cumulative experiments of [$^{18}$F]-FLT, it might be because that iodine on the 5th position impede the methylation of thymidylate synthase (TS), and subsequently the enzyme cannot recognize that situation so that the second and third phosphorylation reactions cannot be undergone. Despite of the poor results of [$^{123}$I]-IaraU cellar experiments, the radioactive marking method for uridine analogue has been established. Such an approach as can be put into practice with benefit of significantly reduced production cost, which meets the need of increasing yield and optimizing product quality.

In summary, the present invention provides a probe for iodine-123 marker thymidine analogue [$^{123}$I]-IaraU, which can effectively improve the shortcomings in the prior art. Uridine is used as the raw material for synthesis of [$^{123}$I]-IaraU precursor. At the moderate conditions, the radioactive iodine-123 is marked, with the radioactive specific activity, yield and purity having reached the degree for the use in biological experiments. By means of establishing the radioactive marker of uridine analogue, the production cost can be effectively reduced, which makes this invention more improved, more practical and satisfied to what's in need for the users.

The descriptions illustrated supra set forth simply the preferred embodiments of the present invention; however, the characteristics of the present invention are by no means restricted thereto. All changes, alternations, or modifications conveniently considered by those skilled in the art are deemed to be encompassed within the scope of the present invention delineated by the following claims.

What is claimed is:

1. A tumor radiation probe, having [$^{123}$I]-IaraU of iodine-123 marker thymidine (FLT) analogue, which uses uridine as raw material for synthesis of a precursor of [$^{123}$I]-IaraU and uses iodine-123 for radiological marking, the probe comprising a structure as follows

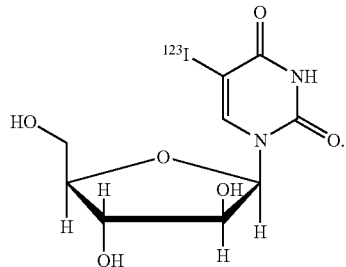

2. The tumor radiation probe of claim 1, wherein the radiological marking is carried out by using radioactive sodium iodide (Na [$^{123}$I]).

3. The tumor radiation probe of claim 1, wherein [$^{123}$I]-IaraU has radiologically chemical purity of higher than 98%.

* * * * *